(12) United States Patent
Shin et al.

(10) Patent No.: US 9,168,095 B2
(45) Date of Patent: Oct. 27, 2015

(54) HIGH-FREQUENCY TREATMENT DEVICE

(71) Applicants: TAEWOONG MEDICAL Co., LTD., Kyunggi-do (KR); Kyong-Min Shin, Kyunggi-do (KR)

(72) Inventors: Kyoung-Min Shin, Kyunggi-do (KR); Chang Il Kwon, Seoul (KR)

(73) Assignees: TAEWOONG MEDICAL Co., LTD, Kyunggi-do (KR); Kyung-Min Shin, Seoul (KR)

( * ) Notice: Subject to any disclaimer, the term of this patent is extended or adjusted under 35 U.S.C. 154(b) by 112 days.

(21) Appl. No.: 13/869,554

(22) Filed: Apr. 24, 2013

(65) Prior Publication Data

US 2013/0345690 A1     Dec. 26, 2013

(30) Foreign Application Priority Data

Jun. 26, 2012   (KR) .................. 10-2012-0068660

(51) Int. Cl.
  *A61B 18/14*     (2006.01)
  *A61B 18/18*     (2006.01)
  *A61B 18/00*     (2006.01)

(52) U.S. Cl.
  CPC .............. *A61B 18/18* (2013.01); *A61B 18/149* (2013.01); *A61B 18/1482* (2013.01); *A61B 2018/00202* (2013.01); *A61B 2018/1405* (2013.01); *A61B 2018/1422* (2013.01); *A61B 2018/1475* (2013.01)

(58) Field of Classification Search
  CPC ................. A61B 18/18; A61B 18/149; A61B 2018/1405; A61B 2018/1422; A61B 2018/1475; A61B 2018/00202; A61B 2018/0091

USPC ................. 606/37, 39, 47, 113; 607/99, 145
  See application file for complete search history.

(56) References Cited

U.S. PATENT DOCUMENTS

| 4,936,301 | A | * | 6/1990 | Rexroth et al. | 606/45 |
| 5,121,686 | A | * | 6/1992 | Schonlau et al. | 92/163 |
| 5,304,893 | A | * | 4/1994 | Nieda | 313/631 |
| 6,048,340 | A | | 4/2000 | Miyagi | |
| 6,551,298 | B1 | * | 4/2003 | Zhang et al. | 604/403 |
| 6,767,348 | B2 | | 7/2004 | Nakada et al. | |
| 7,052,495 | B2 | * | 5/2006 | Smith | 606/47 |

(Continued)

FOREIGN PATENT DOCUMENTS

| JP | 4329944 | 11/1992 |
| JP | 2005-007161 | 1/2005 |

(Continued)

*Primary Examiner* — Michael Peffley
*Assistant Examiner* — Thomas Giuliani
(74) *Attorney, Agent, or Firm* — IP & T Group LLP (57) ABSTRACT

A high-frequency treatment device includes a tubular body having a front end portion and a rear end portion; an operating handle having a high-frequency port and a main push rod extending through the body, the operating handle slidably fitted to the body; a front tube having a rear end portion connected to the front end portion of the body; an auxiliary push rod rotatably connected to the main push rod, the auxiliary push rod extending into the front tube; a wire fixed to the auxiliary push rod, the wire extending through the front tube; a rotary knob rotatably attached to the body, the rotary knob configured to rotate together with the auxiliary push rod and the wire; and an arc-shaped knife fixed to the wire and connected to the high-frequency port of the operating handle via the wire, the auxiliary push rod and the main push rod.

7 Claims, 10 Drawing Sheets

(56) References Cited

U.S. PATENT DOCUMENTS

| | | | |
|---|---|---|---|
| 7,618,416 B2 * | 11/2009 | Ono et al. | 606/45 |
| 8,226,646 B2 | 7/2012 | Konishi et al. | |
| 2004/0210284 A1 * | 10/2004 | Okada | 607/96 |
| 2007/0016184 A1 * | 1/2007 | Cropper et al. | 606/41 |
| 2008/0221567 A1 * | 9/2008 | Sixto et al. | 606/41 |
| 2010/0331742 A1 * | 12/2010 | Masuda | 601/2 |
| 2013/0041373 A1 * | 2/2013 | Laufer | 606/47 |

FOREIGN PATENT DOCUMENTS

| | | |
|---|---|---|
| JP | 4315725 | 8/2009 |
| JP | 4794564 | 10/2011 |
| JP | 2012-120881 | 6/2012 |

\* cited by examiner

HIGH-FREQUENCY TREATMENT DEVICE

CROSS-REFERENCE TO RELATED APPLICATIONS

The present application claims priority of Korean Patent Application no. 10-2012-0068660, filed on Jun. 26, 2012, which is incorporated herein by reference in its entirety.

FIELD OF THE INVENTION

The present invention relates to a high-frequency treatment device and, more specifically, to a high-frequency treatment device capable of marking a tissue region to be removed, enlarging an excision area to thereby shorten an operation time and rotating to cleanly scrape out an excised surface.

BACKGROUND OF THE INVENTION

In the past, a treatment for excising a living tissue such as mucosa or the like has been performed by inserting an endoscope into a body and putting a treatment tool into the body through a channel of the endoscope. In this excising treatment, use is made of, e.g., a high-frequency treatment device as disclosed in JP Publication No. 4-329944 (JP4-329944A).

The high-frequency treatment device disclosed in JP4-329944A includes an elongated insertion portion and a front operation portion. The insertion portion is inserted into a body through a channel of an endoscope. The operation portion is connected to a base end of the insertion portion. The insertion portion includes a flexible tube and an operating wire. The operating wire is inserted into the flexible tube in an axially movable manner. A needle-shaped knife portion (an electrode portion) extending in an axial direction is provided in the tip end portion of the operating wire. The operation portion is provided with an operating handle. The operating wire is axially moved by the operation of the operating handle. A high-frequency current can be supplied to the knife portion.

The operating wire is axially moved during the operation of the operating handle. By way of the operating wire, the knife portion is displaced from a storage position in which the knife portion stays within the flexible tube to a use position in which the knife portion protrudes out of the flexible tube. In a state that the knife portion protrudes from the flexible tube into the use position, a high-frequency current is supplied to the knife portion, thereby cauterizing and excising a living tissue with the knife portion.

The high-frequency treatment device as disclosed in JP4-329944A includes a liquid supply means installed in the base end portion of the insertion portion to supply a liquid chemical or the like. The liquid chemical is supplied from the liquid supply means to the tip end of the flexible tube through the flexible tube and can be discharged to the outside from a tip end opening of the flexible tube.

Another high-frequency treatment device includes a bent section formed by bending a tip end of a needle-shaped knife portion (an electrode portion). In this high-frequency treatment device, a living tissue is cauterized and excised while hooking and lifting the living tissue with the bent section of the knife portion.

Another high-frequency treatment device includes a disc-like electrode section arranged at a tip end of a needle-shaped knife portion (an electrode portion). In this high-frequency treatment device, a living tissue is cauterized and excised while hooking and lifting the living tissue with the disc-like electrode section.

If a living tissue is excised through the use of the high-frequency treatment devices referred to above, it is sometimes the case that an incised region bleeds during incision. In this case, the following countermeasures are taken in the respective high-frequency treatment devices.

In case of the high-frequency treatment device disclosed in JP4-329944A, the high-frequency treatment device currently in use is first taken out from a channel of an endoscope. Then, a hemostatic treatment is carried out by inserting a blood-stanching implement into the channel of the endoscope. Once the bleeding is stopped, the blood-stanching implement is replaced by the high-frequency treatment device.

In case of the high-frequency treatment device, the bent section of the tip end of the knife portion or the tip end surface of the disc is pressed against a bleeding point and is supplied with a high-frequency current. As a consequence, blood is coagulated and stanched.

In the event that a large amount of blood is bled from an incised region when a living tissue is incised with a high-frequency treatment device, the bleeding point becomes unclear, making it difficult to perform a hemostatic treatment. In this case, there is a need to wash a bleeding region to clarify the bleeding point. In a high-frequency treatment device having no liquid supply function, however, the treatment device should be first recovered from a channel of an endoscope. Then, a washing solution should be supplied through the channel of the endoscope to wash the bleeding region. Alternatively, a washing liquid should be supplied by replacing a washing catheter arranged within the channel of the endoscope. For that reason, the operation is hard to perform and the time required for high-frequency treatments may possibly become longer.

In case of the high-frequency treatment device of JP4-329944A in which the liquid supply means is arranged in the base end portion of the insertion portion and in which the flexible tube of the insertion portion is opened at the tip end thereof. It is possible to supply a liquid chemical through the flexible tube. However, if the tip end of the flexible tube is opened into a large size, the knife portion is unstably supported and may possibly wobble.

In the high-frequency treatment device having the bent portion or the disc installed at the tip end of the knife portion, if the knife portion is unstably supported, there is likelihood that the bent portion or the disc partially protrudes outward from the outer circumferential surface of the flexible tube when the knife portion is introduced into the flexible tube. The portion protruding outward from the outer circumferential surface of the flexible tube may possibly injure a channel wall when the knife portion is inserted into the endoscope.

According to a technology of JP Patent Application No. 2003-113164 (JP Patent No. 4315725) entitled "high-frequency knife" rod-shaped portion extending in an axial direction of a flexible sheath is installed in an electrode portion. A sliding hole into which the rod-shaped portion is inserted to move forward and backward in the axial direction of the flexible sheath and a liquid supply opening into which the rod-shaped portion cannot be inserted are formed in an insulating chip closing the tip end portion of the flexible sheath.

However, the conventional high-frequency knife is formed into a triangular shape. This poses a problem in that the high-frequency knife has a difficulty in marking a cut region and cannot cleanly scrape out a cut surface.

According to a technology of JP Patent Application No. 2003-146476 UP Publication No. 2005-007161) entitled "EMR treatment implement and EMR device," a peeling and lifting member is provided in an EMR treatment implement and an EMR device for excising a lesion while alleviating complications and patient's burdens in endoscopic mucosal resection. A target excision portion including a lesion is peeled and separated by the peeling and lifting member. Then, the lesion is lifted up. This helps shorten the time required for operations.

However, the conventional EMR treatment implement and the conventional EMR device are not capable of keeping the lesion in a peeled state during an incising operation. Since the knife is formed into a needle shape, the excision region becomes narrow. This leads to a prolonged operation time. Inasmuch as the tube is not transparent, there is posed a problem in that it is difficult to clearly determine the inward and outward movement of the knife.

According to a technology of JP Patent Application No. 2005-278473 (JP Patent No. 4794564) entitled "treatment implement for endoscopes," ridge portions and valley portions are formed in the tip end portion and the base end portion of the treatment implement. A plurality of cutters is installed in the valley portions. There is also installed a selector means for selecting one cutter to be used from the plurality of cutters.

In this conventional treatment implement for endoscopes, however, each of the cutters is formed into a shape similar to an irregular elliptical sphere. Therefore, an excision area is unnecessarily increased when excising a lesion. This poses a problem in that the pain felt by a patient is increased and a normal tissue is removed together with a lesion.

According to a technology of JP Patent Application No. 2010-018130 (JP Publication No. 2012-120881) entitled "treatment implement for endoscopes," a triangular electrode portion includes a first electrode having a triangular chip radially extending from a distal end toward a proximal end.

Since the electrode portion is formed into a triangular shape in this conventional treatment implement for endoscopes, the tube should be laid down when excising a lesion. Another problem lies in that the pointed vertex may make contact with a normal tissue and may injure the normal tissue.

With the conventional technologies referred to above, the lesion is not cleanly cut but is irregularly excised. This poses a problem in that an extended period of time is required for the cut surface to restore after the excising operation.

SUMMARY OF THE INVENTION

In view of the problems inherent in the prior art, it is an object of the present invention to provide a high-frequency treatment device capable of excising a wide area of living tissue with a wide-edge knife.

Another object of the present invention is to provide a high-frequency treatment device capable of, through the use of an arc-shaped knife, cleanly scraping out a cut surface from which a lesion is excised.

A further object of the present invention is to provide a high-frequency treatment device capable of rotating an arc-shaped knife and freely controlling the advancing direction of the arc-shaped knife even when a lesion has an irregular edge.

In accordance with the present invention, there is provided a high-frequency treatment device for excising a lesion tissue from a normal tissue, including: a tubular body having a front end portion and a rear end portion, an operating handle having a high-frequency port, the operating handle slidably fitted to the body, the operating handle including a main push rod extending through the body, a front tube having a rear end portion connected to the front end portion of the body, an auxiliary push rod rotatably connected to the main push rod, the auxiliary push rod extending into the front tube, a wire fixed to the auxiliary push rod, the wire extending through the front tube, a rotary knob rotatably attached to the body, the auxiliary push rod slidably fitted to the rotary knob, the rotary knob configured to rotate together with the auxiliary push rod and the wire, and an arc-shaped knife fixed to the wire, the knife connected to the high-frequency port of the operating handle via the wire, the auxiliary push rod and the main push rod.

With the high-frequency treatment device of the present invention, it is possible to simultaneously excise a wide area of living tissue with a wide-edge knife, thereby shortening the time required for an operation.

It is also possible to, through the use of an arc-shaped knife, cleanly scrape out a cut surface from which a lesion is excised. This makes it possible to provide a clean cut surface.

Moreover, it is possible to rotate an arc-shaped knife and to freely control the advancing direction of the arc-shaped knife even when a lesion has an irregular edge.

In addition, it is possible to supply a saline solution the a tube under an appropriate pressure and to inject a saline solution into an incised tissue gap, thereby preventing re-adherence of an incised tissue, peeling and lifting up the incised tissue and making it easy to remove the incised tissue.

BRIEF DESCRIPTION OF THE DRAWINGS

The above and other objects and features of the present invention will become apparent front the following description of preferred embodiments, given in conjunction with the accompanying drawings.

DETAILED DESCRIPTION OF THE PREFERRED EMBODIMENTS

One preferred embodiment, of the present invention will now be described in detail with reference to the accompanying drawings.

Referring to FIGS. 1 to 9, there is shown a high-frequency treatment device that lifts up a lesion tissue by injecting a saline solution and then removes the lesion tissue from a normal tissue with high-frequency waves. In the high-frequency treatment device 100, an operating handle 20 is movable along a body 10 of an operating unit 80. An arc-shaped knife 41 is moved forward or backward by the operation of the operating handle 20. The orientation of the knife 41 is changed by rotating a rotary knob 60. Thus, the high-frequency treatment device 100 can excise an irregularly-shaped lesion along an edge thereof and can make a clean cut surface.

Figure 1:
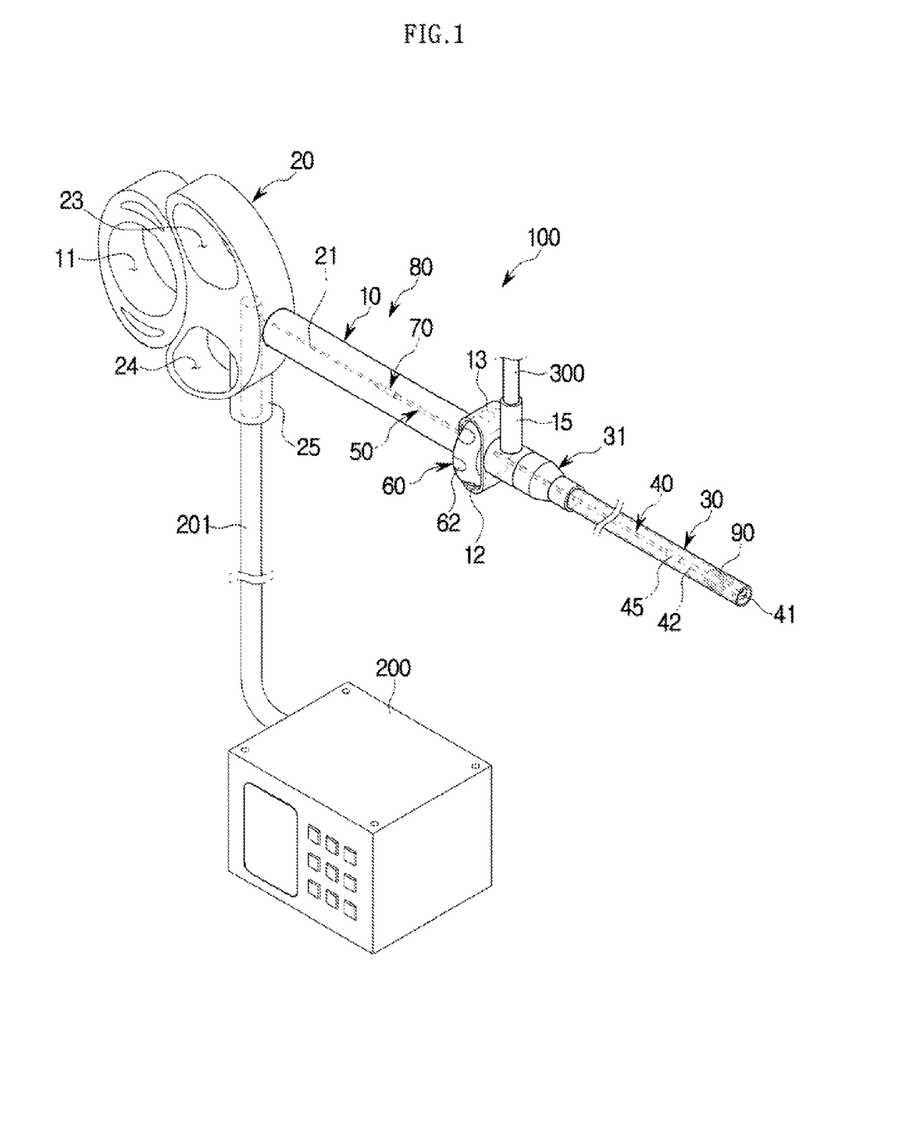
FIG. 1 is a schematic perspective view showing a high-frequency treatment device according to the present invention.

In the operating unit 80, the operating handle 20 having a high frequency port 25 can move forward and backward along the tubular body 10 having a saline solution inlet port 15 fainted at the front end portion thereof. A main push rod 21 extending through the body 10 is connected to the operating handle 20.

The body 30 has an elongated tubular shape. The body 10 has a first finger hole 11 into which the thumb of an operator can be inserted.

A knob bracket 13 partially surrounding the rotary knob 60 is arranged at the front end of the body 10. One or more engaging projections 14 protrude from one inner wall of the knob bracket 13.

The saline solution inlet port 15 is one-piece formed in the front end portion of the body 10. The saline solution inlet port 15 communicates with an internal space 21a of the body 10 through which the main push rod 21 extends. Thus, a saline solution can flow through the internal space 21a of the body 10.

A seal ring 21b through which the main push rod 21 extends is arranged within the body 10 between the rotary knob 60 and the saline solution inlet port 15, thereby preventing a saline solution from flowing toward the rotary knob 60.

While the knob bracket 13 is provided with two engaging projections 14 in the present embodiment, the number of the engaging projections 14 is not limited to two but may be one or more than two.

The knob bracket 13 is formed into a substantially elliptical tube shape to have a pair of end openings 12. The knob bracket 13 is made of, e.g., a synthetic resin, to have a reduced thickness.

The high-frequency port 25 is supplied with high-frequency waves from a high-frequency generator 200 used for medical purposes. The high-frequency generator 200 is connected to the high-frequency port 25 via a high-frequency supply line 201. The high-frequency waves are transmitted from the high-frequency port 25 to the knife 41 via the main push rod 21, an auxiliary push rod 50 and a wire 40.

The operating handle 20 is fitted to the outer circumferential surface of the body 10 so as to slide forward and backward along the longitudinal direction of the body 10. The operating handle 20 has second and third finger holes 23 and 24.

Figure 2:
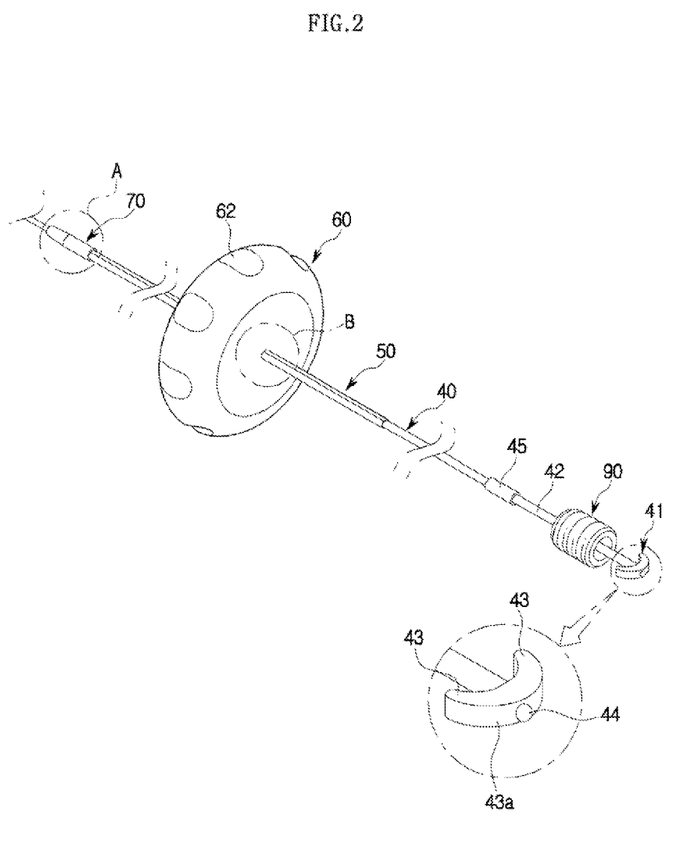
FIG. 2 is a partial perspective view showing a rotary knob, an auxiliary push rod and a knife of the high-frequency treatment device.

The auxiliary push rod 50 having an engaging surface 51 is rotatably connected to the front end of the main push rod 21 of the operating handle 20. The engaging surface 51 of the auxiliary push rod 50 is formed of flat upper and lower surfaces and round left and right surfaces.

Figure 3:
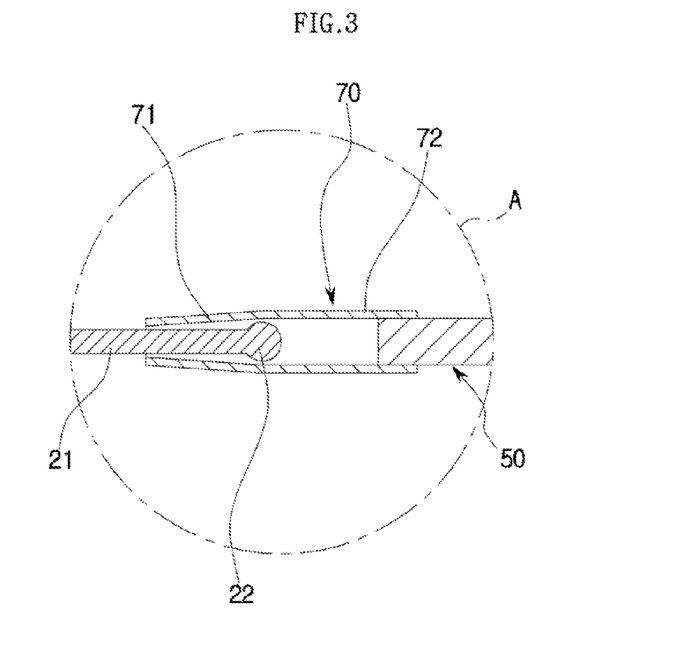
FIG. 3 is a partially enlarged section view of the part indicated by "A" in FIG. 2, showing the auxiliary push rod connected to a connecting tube.

A ball head 22 larger in diameter than the main push rod 21 is formed at the front end of the main push rod 21 to enable relative rotation of the main push rod 21 and the auxiliary push rod 50.

A connecting tube 70 is arranged between the main push rod 21 and the auxiliary push rod 50 so as to interconnect the main push rod 21 and the auxiliary push rod 50. The connecting tube 70 includes a tapering end portion 71 having an inner diameter smaller than the diameter of the ball head 22 and a connecting end portion 72 having an inner diameter larger than the diameter of the ball head 22. The main push rod 21 is inserted through the tapering end portion 71 so that the ball head 22 can be caught by the tapering end portion 71 against removal. The auxiliary push rod 50 is fixed to the connecting end portion 72 of the connecting tube 70. The auxiliary push rod 50 and the connecting tube 70 can rotate together with respect to the main push rod 21.

A front tube 30 is connected to the front end of the body 10. The wire 40 connected to the front end of the auxiliary push rod 50 extends through the front tube 30. In order to transfer the torque of the rotary knob 60 to the knife 41, the wire 40 is formed of, e.g., a steel strand which has flexibility.

The body 10 has a male thread portion 18 and a slant tip end portion 16a whose diameter grows smaller forward. The rear end portion of the front tube 30 is press-fitted to the slant tip end portion 16a of the body 10. A sleeve 31 is threadedly coupled to the body 10. The sleeve 31 includes a female thread portion 31a threadedly coupled to the male thread portion 16, a slant pressing portion 31b configured to press the rear end portion of the front tube 30 against the slant tip end portion 16a of the body 10, and a cover portion 31c arranged to partially surround the front tube 30. When threadedly coupling the female thread portion 31a of the sleeve 31 to the male thread portion 16 of the body 10, the slant pressing portion 31b of the sleeve 31 presses the rear end portion of the front tube 30 against the slant tip end portion 16a of the body 10. Thus, the front tube 30 is connected to the body 10 in a fluid-tight manner. At least the front end portion of the front tube 30 is made transparent so that an operator can observe the motion of the knife 41.

The saline solution inlet port 15 is configured to supply a saline solution in order to space a lesion tissue apart from a normal tissue before excising the lesion tissue. A saline solution supply tube 300 is connected to the saline solution inlet port 15. The saline solution is supplied through the saline solution supply tube 300 prior to performing a marking operation.

The wire 40 is fixed to the front end of the auxiliary push rod 50. The knife 41 having an arc shape is connected to the tip end of the wire 40 of the operating unit 80.

The knife 41 includes a rod-shaped knife shank 42 connected to the wire 40, an arc-shaped blade 43 one-piece formed with the knife shank 42, and a spear head 44 protruding forward from the center of the blade 43.

The spear head 44 is configured to, using high-frequency waves, leave point-like marks along an edge of a lesion so as to indicate an excising region to be excised by the knife 41. The blade 43 has a curved surface 43a configured to, using high-frequency waves, excise a lesion tissue along the marks formed in advance by the spear head 44.

The spear head 44 is preferably formed into a substantially hemispherical shape so that the spear head 44 can smoothly form the marks indicating the excising region.

Figure 4:
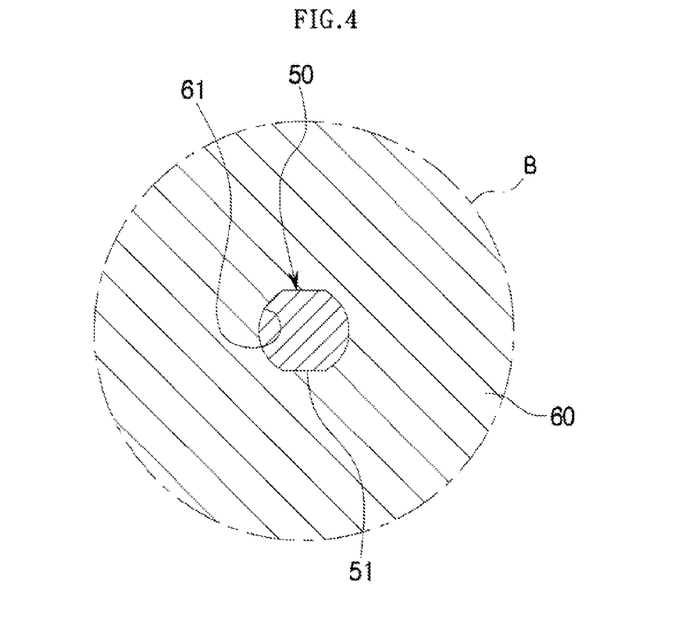
FIG. 4 is a section view of the part indicated by "B" in FIG. 2, showing the auxiliary push rod fitted to the rotary knob.

The rotary knob 60 has a through-hole 61 into which the auxiliary push rod 50 is inserted. A plurality of anti-slip grooves 62 is formed on the outer circumferential surface of the rotary knob 60 to prevent slip of a finger when rotating the rotary knob 60 with the finger.

Figure 5:
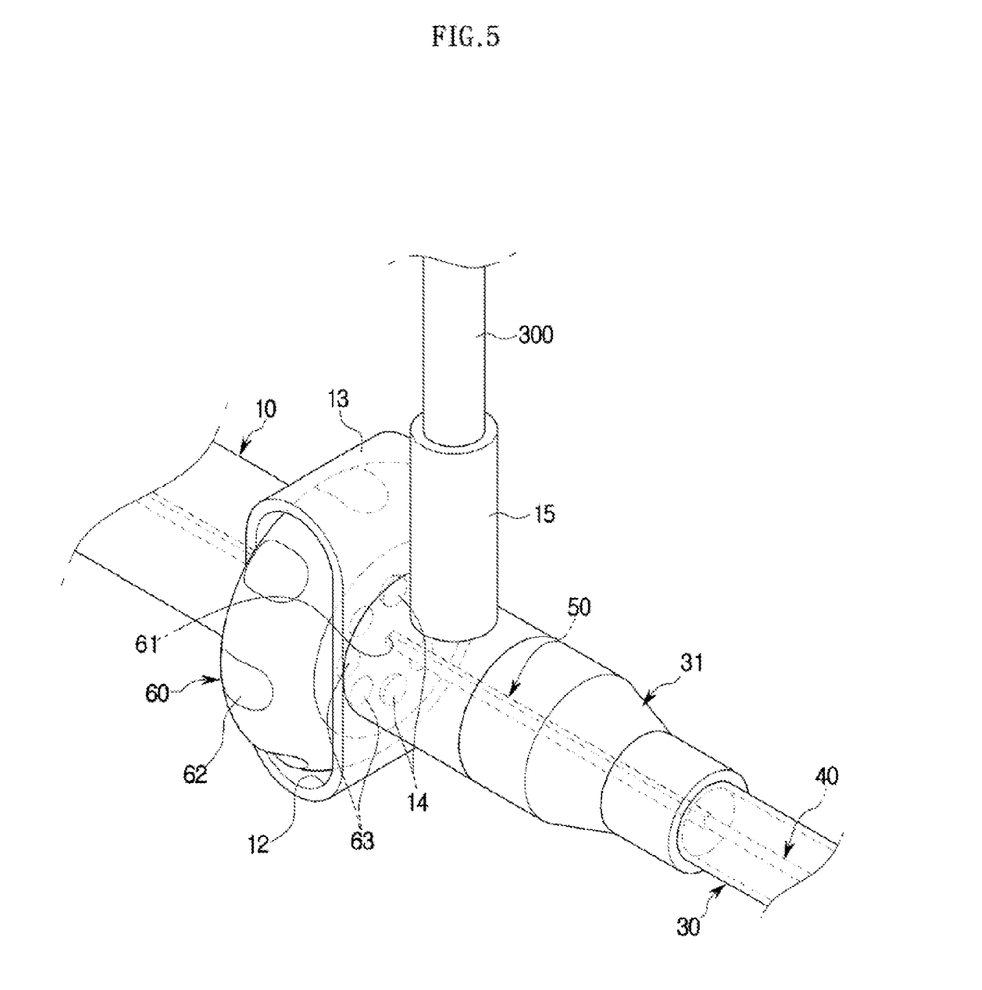
FIG. 5 is a partial perspective view showing a state that the engaging projections of a knob bracket engage with engaging grooves of the rotary knob.

The rotary knob 60 includes a plurality of engaging grooves 63 formed on one side surface of the rotary knob 60 and arranged at a regular interval along a circumferential direction of the rotary knob 60.

Figure 7:
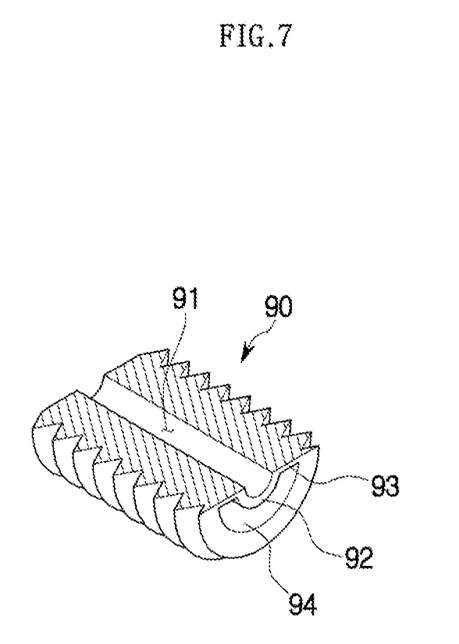
FIG. 7 is a partially cutaway perspective view showing a stopper.

A cylindrical stopper 90 is arranged within and threadedly coupled to the front tube 30. The knife shank 42 of the knife 41 extending through the stopper 90 is connected to the wire 40 by virtue of a connecting sleeve 45. As best shown in FIG. 7, the stopper 90 includes a through-hole 91 through which the knife shank 42 extends, an inner wall 92 defining the through-hole 91, an outer wall larger in diameter than the inner wall 92, a plurality of radial ribs 93 interconnecting the inner wall 92 and the outer wall, and a saline solution path 94 defined between the inner wall 92 and the outer wall.

Figure 11:
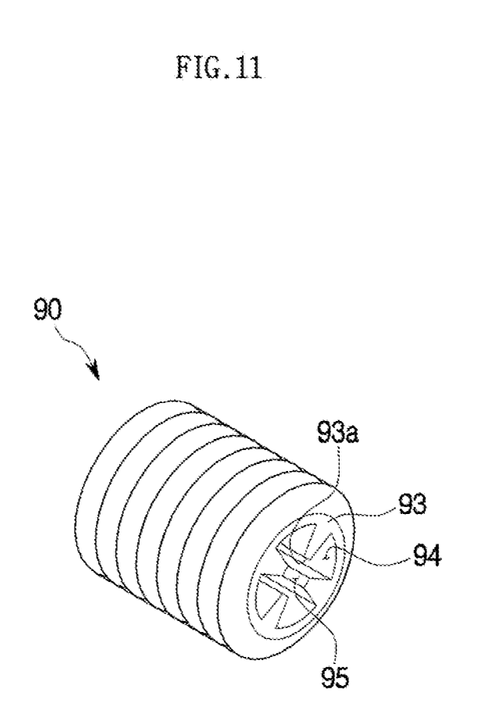
FIG. 11 is a perspective view showing a modified example of the stopper.

FIG. 11 shows a stopper 90 according to a modified example. The stopper 90 of the modified example includes a plurality of ribs 93 protruding radially inward from an inner surface of the stopper 90, a plurality of saline solution paths 94 arranged between the ribs 93 along a circumferential direction, and a central through-hole 95 defined between tip ends 93a of the ribs 93. The rod-like knife shank 42 extends through the central through-hole 95. The tip ends 93a of the ribs 93 are formed into a concave shape so as to smoothly guide the movement of the rod-like knife shank 42.

The saline solution supplied via the saline solution supply tube 300 and the saline solution inlet port 15 flows through the front, tube 30 and the saline solution paths 94 and comes out from the tip end of the front tube 30.

Figure 8:
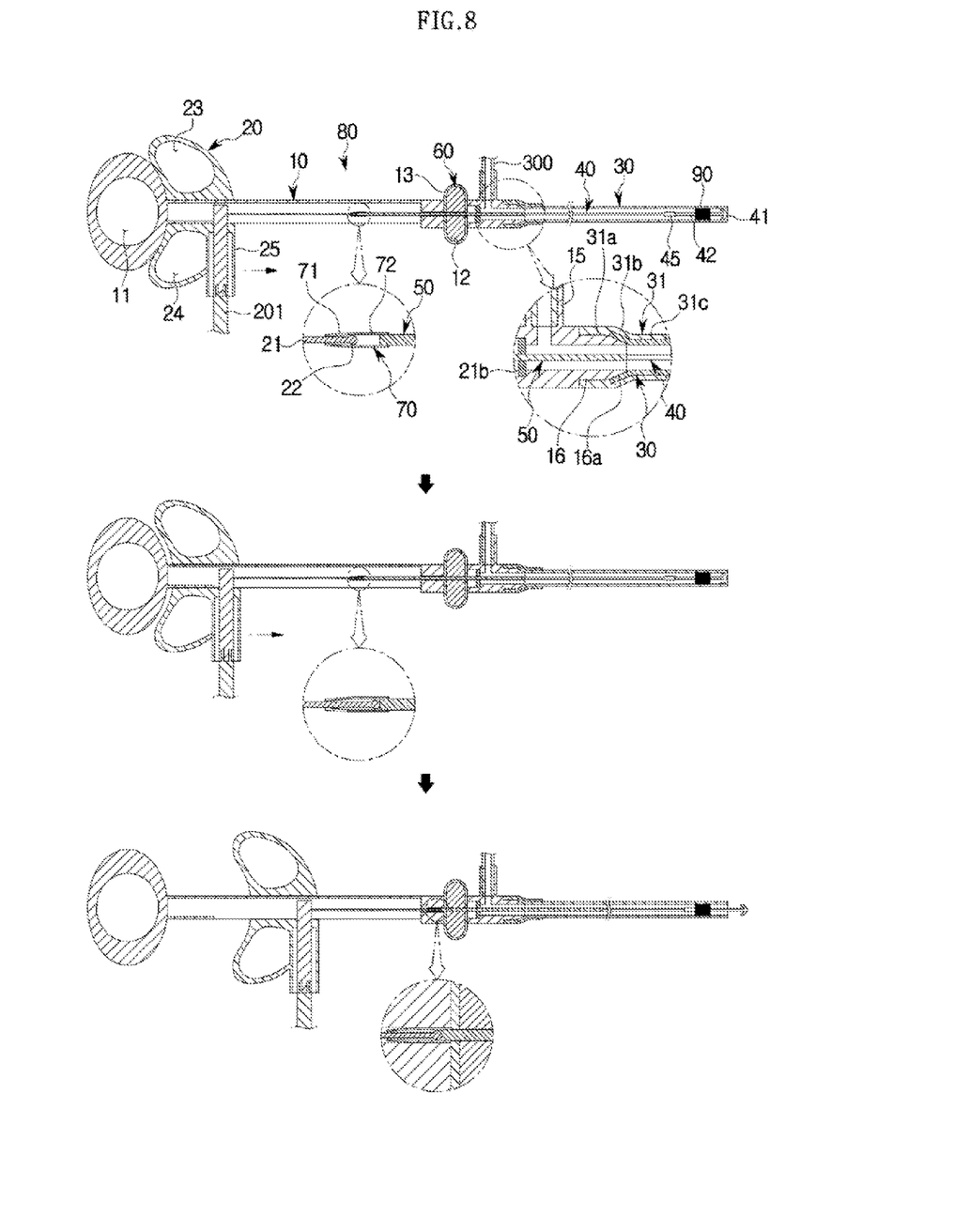
FIG. 8 is an operation view showing the operation of an operating handle of the high-frequency treatment device and the resultant movement of a wire and a knife.

As the operating handle 20 is moved forward together with the main push rod 21, the auxiliary push rod 50 and the wire 40, the connecting sleeve 45 comes into contact with the rear end of the stopper 90, thereby limiting the protruding length of the knife 41.

Figure 9:
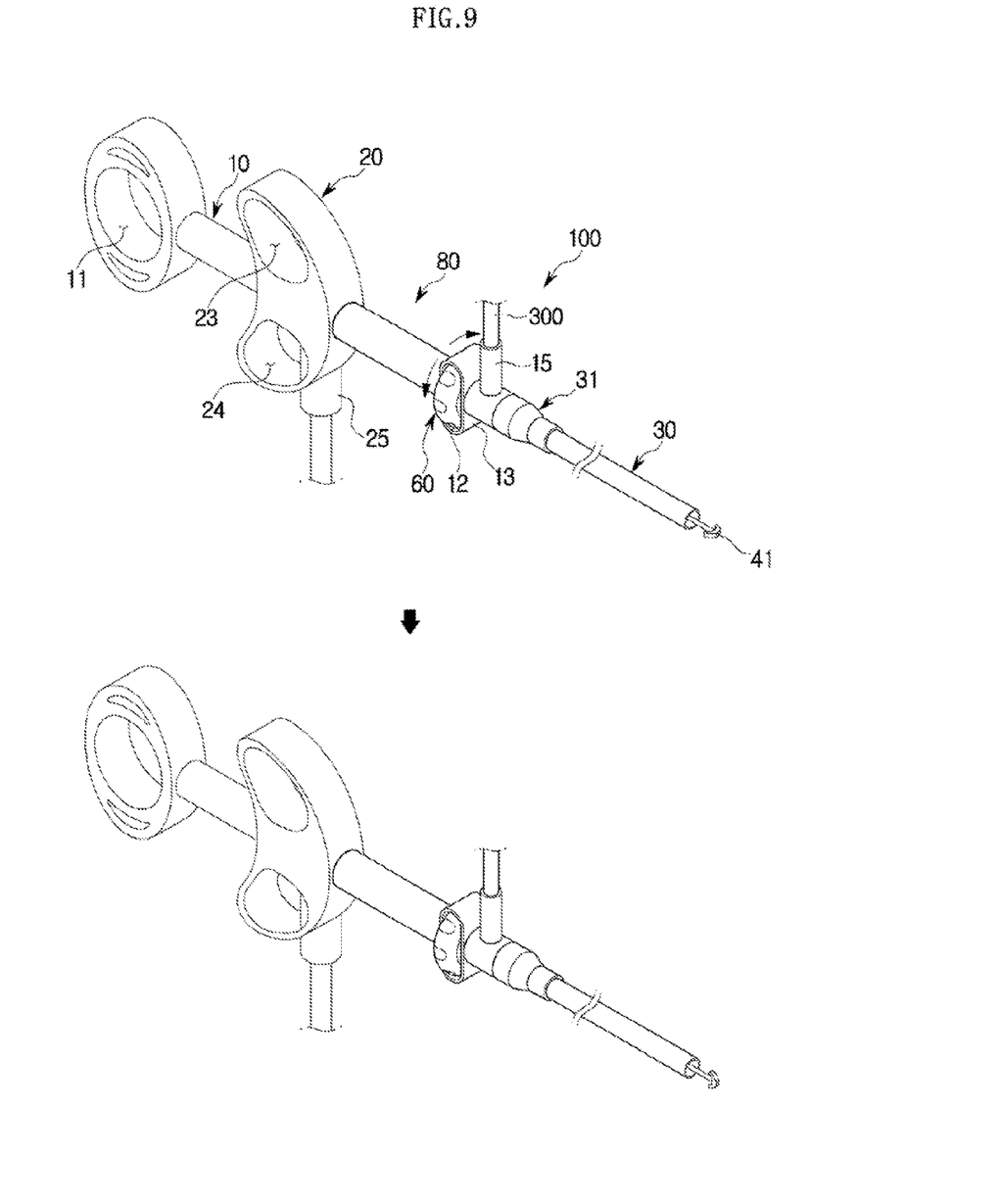
FIG. 9 is an operation view showing how to change the orientation of the knife by rotating the rotary knob.

More specifically, if the operating handle 20 is moved forward or backward, the main push rod 21, the auxiliary push rod 50, the wire 40 and the knife 41 are also moved forward or backward together with the operating handle 20. At this time, the auxiliary push rod 50 slides along the through-hole 61 of the rotary knob 60. Upon rotating the rotary knob 60, the auxiliary push rod 50 and the wire 40 are rotated together with the knife 41.

Next, description will be made on the operation performed by the high-frequency treatment device 100.

Referring to FIGS. 1 to 10, the high-frequency treatment device 100 is used in, e.g., excising a lesion tissue such as a gastric ulcer tissue which may be generated after removal of cancer cells.

In operation, the thumb of an operator is inserted into the first finger hole 11 of the body 10. The index finger and the middle finger are inserted into the second and third finger holes 23 and 24 of the operating handle 20. If the operating handle 20 is moved backward with respect to the body 10, the knife 44 is retracted into the front tube 30.

Then, the high-frequency supply line 201 is connected to the high-frequency port 25 of the operating handle 20 so that, the high-frequency waves can be supplied from the high-frequency generator 200 to the knife 41 via the main push rod 21, the auxiliary push rod 50 and the wire 40. Thereafter, the saline solution supply tube 300 is connected to the saline solution inlet port 15 so that a saline solution can be supplied to a lesion tissue through the front tube 30.

Figure 10:
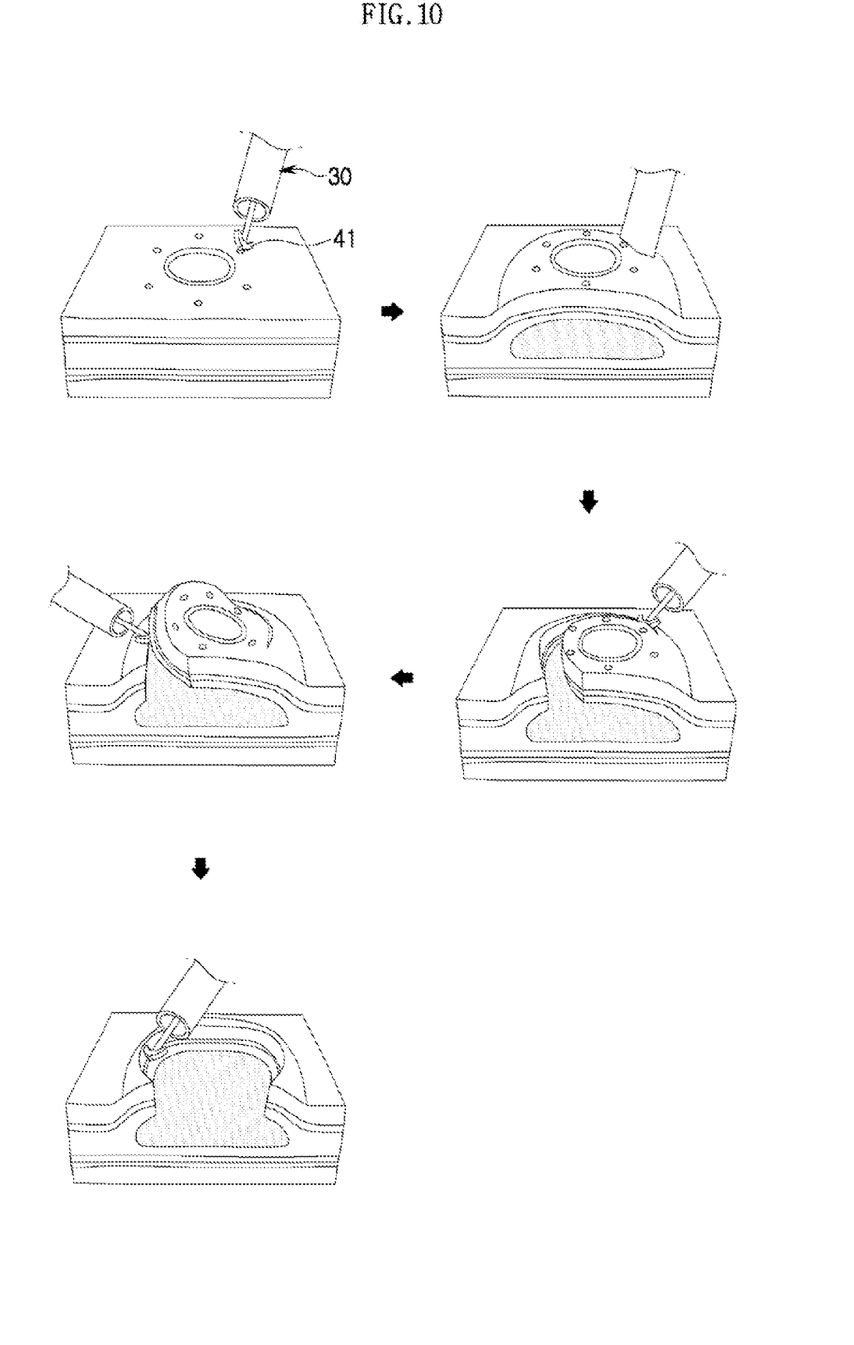
FIG. 10 is a view illustrating a lesion excising process performed through the use of the high-frequency treatment device.

An endoscope is inserted into the body of a patient to visually confirm the position of a gastric ulcer tissue to be excised. Then, the front tube 30 of the high-frequency treatment device 100 is inserted into the body of a patient.

The tip end of the front tube 30 is moved toward a lesion tissue while observing the movement of the front tube 30 through the use of the endoscope. The high-frequency generator 200 is energized to supply high-frequency waves to the knife 41 via the main push rod 21, the auxiliary push rod 50 and the wire 40.

The operating handle 20 is moved forward together with the main push rod 21, the auxiliary push rod 50 and the wire 40 so that the knife 41 can come out from the front tube 30. In this state, dot-like marks are formed along the edge of a lesion through the use of the spear head 44 of the knife 41.

Since the front tube 30 is at least partially transparent, an operator can visually confirm the movement of the knife 41 within the front tube 30 through the use of the endoscope.

Thereafter, the tissue surrounding a lesion is partially incised by moving the knife 41 to reach a submucous layer lying below a raucous layer. The tip end of the front tube 30 is brought into contact with the incised portion. In this state, the saline solution is supplied through the front tube 30 and is injected into a clearance created by incision, thereby preventing re-adherence of an incised tissue, peeling and lifting up the incised tissue and making it easy to remove the incised tissue.

Alternatively, the tissue surrounding a lesion may be partially incised by moving the knife 41 to reach a submucous layer lying below a mucous layer. Then, the knife 41 may be retracted into the front tube 30. The tip end of the front tube 30 may be brought into contact with the incised portion. In this state, the saline solution may be supplied through the front tube 30 and may be injected into a clearance created by incision, thereby preventing re-adherence of an incised tissue, peeling and lifting up the incised tissue and making it easy to remove the incised tissue.

Next, the high-frequency generator 200 is energized to supply high-frequency waves to the knife 41. In this state, the curved surface 43a of the knife 41 is brought into contact with the mucous layer of the lesion along the marks. At this time, the mucous layer and the submucous layer are partially cut by the curved surface 43a of the knife 41 with the aid of the high-frequency waves.

The depth of incision can be controlled by adjusting the advancing distance of the knife 41 which is moved by the operating handle 20. The maximum advancing distance of the knife 41 is limited by the connecting sleeve 45 that makes contact with the stopper 90 when the knife 41 is moved forward by the maximum advancing distance.

The reason for limiting the maximum advancing distance of the knife 41 is to prevent the knife 41 from advancing too far and injuring a normal tissue and to prevent the gastric mucosa from being penetrated by the knife 41.

The lesion is excised by moving the knife 41 along the edge of the lesion. If the lesion has an irregular shape, the orientation of the curved surface 43a of the knife 41 is changed by rotating the rotary knob 60. This makes if possible to easily control the advancing direction of the knife 41.

Upon rotating the rotary knob 60, the auxiliary push rod 50 fitted to the through-hole 61 of the rotary knob 60 is rotated together with the rotary knob 60. Since the auxiliary push rod 50 is rotatably connected to the main push rod 21 through the connecting tube 70, the main push rod 21 does not rotate even if the auxiliary push rod 50 makes rotation. Only the auxiliary push rod 50 and the wire 40 are rotated together with the knife 41.

Figure 6:
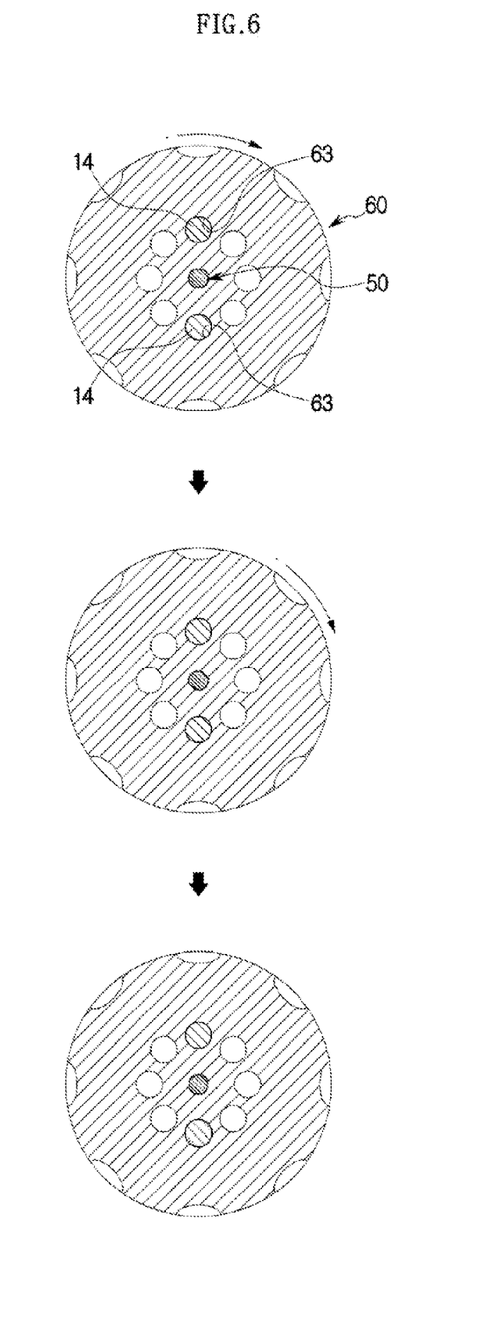
FIG. 6 is an operation view showing how the engaging projections come into engagement with the engaging grooves during rotation of the rotary knob.

When the orientation of the knife 41 is changed by rotating the rotary knob 60, the engaging projections 14 of the knob bracket 13 come into engagement with the engaging grooves 63 of the rotary knob 60. This prevents the knife 41 from returning back to the original angular position by the restoring force of the wire 40.

Since the knob bracket 13 is formed to have a reduced thickness and is elastically deformable, the rotary knob 60 can push the knob bracket 13 outward when the rotary knob 60 is rotated with respect to the knob bracket 13. If the engaging projections 14 of the knob bracket 13 come into engagement with the engaging grooves 63 of the rotary knob 60, the knob bracket 13 is returned back to the original position by the elastic restoration force thereof.

Thus, there is no need to hold the rotary knob 60 to fix the knife 41 in a specific angular position. This makes it easy to perform an operation.

After the lesion is excised by the knife 41, the gastric mucosa may not be smoothly cut due to the irradiation of the high-frequency waves. In this case, the irregularly cut edge of the gastric mucosa can be cleanly scraped with the curved surface 43a of the knife 41. This makes it possible to prevent contamination of the cut edge of the gastric mucosa and to accelerate healing of the excised region.

With the high-frequency treatment device of the present invention, a lesion can be easily and rapidly excised through the use of the knife 41 having the curved surface 43a. Therefore, as compared with a conventional high-frequency treatment device having a needle-shaped knife, it is possible to shorten the time required for an operation, thereby alleviating the burdens borne by an operator and a patient.

While one preferred embodiment of the invention has been described hereinabove, the present invention is not limited thereto. It is to be understood that various changes and modifications may be made without departing from the scope of the invention defined in the claims.

What is claimed is:

1. A high-frequency treatment device for excising a lesion tissue from a normal tissue, comprising:
    a tubular body having a front end portion and a rear end portion;
    an operating handle having a high-frequency port, the operating handle slidably fitted to the body, the operating handle including a main push rod extending through the body;
    a front tube having a front end portion and a rear end portion connected to the front end portion of the body;
    an auxiliary push rod having engagement faces on an outer circumference and is rotatably connected to the main push rod, the auxiliary push rod extending into the front tube;
    a wire fixed to the auxiliary push rod, the wire extending through the front tube;
    a rotary knob having an engagement hole in its hub formed to accept the engagement faces of the auxiliary push rod and rotatably attached to the body, the auxiliary push rod slidably fitted to the rotary knob so that the engagement faces of the auxiliary push rod engage the engagement hole of the hub when the operating handle slides toward the front end portion of the tubular body thereby enabling the auxiliary push rod, the rotary knob and the wire to rotate together; and
    an arc-shaped knife that retracts into the front end portion of the front tube when the operating handle slides away from the front end portion of the tubular body and protrudes out of the front end portion of the front tube when the operating handle slides toward the front end portion of the tubular body and is fixed to the wire so that the arc-shaped knife rotates when the engagement faces of the auxiliary push rod engage the engagement hole of the rotary knob's hub, wherein the arc-shaped knife is connected to the high-frequency port of the operating handle via the wire, the auxiliary push rod and the main push rod;
    wherein the body includes a saline solution inlet port formed in the front end portion of the body.

2. The high-frequency treatment device of claim 1, further comprising:
    a connecting tube arranged to interconnect the main push rod and the auxiliary push rod, the main push rod including a ball head formed at a front end of the main push rod, the connecting tube including a tapering end portion having an inner diameter smaller than a diameter of the ball head and a connecting end portion having an inner diameter larger than the diameter of the ball head, the main push rod inserted into the tapering end portion such that the ball head is caught by the tapering end portion, the auxiliary push rod fixed to the connecting end portion of the connecting tube.

3. The high-frequency treatment device of claim 1, wherein the knife includes a rod-shaped knife shank connected to the wire, an arc-shaped blade formed integrally with the knife shank and a spear head protruding forward from a center of the blade.

4. The high-frequency treatment device of claim 3, further comprising:
    a cylindrical stopper arranged within and threadedly coupled to the front tube, the stopper configured to limit movement of the knife shank.

5. The high-frequency treatment device of claim 4, wherein the stopper includes a through-hole through which the knife shank extends, an inner wall defining the through-hole, an outer wall larger in diameter than the inner wall, a plurality of radial ribs interconnecting the inner wall and the outer wall, and a saline solution path defined between the inner wall and the outer wall.

6. The high-frequency treatment device of claim 1, wherein the front tube is at least partially transparent.

7. The high-frequency treatment device of claim 1, further comprising:
    a knob bracket fixed to the body and configured to partially surround the rotary knob, the rotary knob including a plurality of engaging grooves formed on one side surface of the rotary knob and arranged along a circumferential direction of the rotary knob, the knob bracket including at least one engaging projection engageable with at least one of the engaging grooves of the rotary knob.

\* \* \* \* \*